(12) United States Patent
Vogele

(10) Patent No.: US 10,966,793 B2
(45) Date of Patent: Apr. 6, 2021

(54) DEVICE FOR POSITIONING STERILE INSTRUMENTS

(71) Applicant: ISYS MEDIZINTECHNIK GMBH, Kitzbuhel (AT)

(72) Inventor: Michael Vogele, Schwabmunchen (DE)

(73) Assignee: ISYS MEDIZINTECHNIK GMBH, Kitzbuhel (AT)

(*) Notice: Subject to any disclaimer, the term of this patent is extended or adjusted under 35 U.S.C. 154(b) by 450 days.

(21) Appl. No.: 15/571,643

(22) PCT Filed: May 3, 2016

(86) PCT No.: PCT/EP2016/000722
§ 371 (c)(1),
(2) Date: Jun. 22, 2018

(87) PCT Pub. No.: WO2016/177463
PCT Pub. Date: Nov. 10, 2016

(65) Prior Publication Data
US 2018/0303569 A1 Oct. 25, 2018

(30) Foreign Application Priority Data
May 3, 2015 (DE) .................... 20 2015 003 206.0

(51) Int. Cl.
*A61B 46/10* (2016.01)
*A61M 5/158* (2006.01)
(Continued)

(52) U.S. Cl.
CPC .......... *A61B 46/10* (2016.02); *A61B 17/3403* (2013.01); *A61B 46/20* (2016.02);
(Continued)

(58) Field of Classification Search
CPC ......... A61B 90/40; A61B 46/10; A61B 34/30; A61B 17/3403; A61B 46/20; A61B 10/02;
(Continued)

(56) References Cited

U.S. PATENT DOCUMENTS

2005/0101868 A1 5/2005 Ridley et al.
2014/0166023 A1 6/2014 Kishi
2016/0058513 A1* 3/2016 Giorgi .................... A61B 34/30
606/130

FOREIGN PATENT DOCUMENTS

DE 4403567 A1 8/1995
DE 102009019695 A1 11/2010
(Continued)

OTHER PUBLICATIONS

International Search Report (ISR) with patent family annex dated Jul. 14, 2016 for PCT/EP2016/000722.

*Primary Examiner* — George J Ulsh
(74) *Attorney, Agent, or Firm* — Myers Andras LLP; Joseph C. Andras

(57) ABSTRACT

In order to provide a simple device for positioning sterile instruments, particularly puncture needles, injection needles or surgical probes, with respect to a patient (P), where said device comprises a sheath (3) at least the inside of which is sterile and which at least partially encompasses a sterile instrument (2), as well as at least one gas-tight feedthrough provided on said sheath (3), it is suggested that the sterile instrument (2) has at least one sterile instrument holder (2') and that, by moving the instrument holder (2') outside of the sheath (3), said instrument may be moved in a controlled manner in at least two spatial directions.

11 Claims, 4 Drawing Sheets

(51) Int. Cl.
*A61B 17/34* (2006.01)
*A61B 90/40* (2016.01)
*A61B 46/20* (2016.01)
*A61B 34/30* (2016.01)
*A61B 50/30* (2016.01)
*A61B 10/02* (2006.01)

(52) U.S. Cl.
CPC .............. *A61B 90/40* (2016.02); *A61M 5/158* (2013.01); *A61B 10/02* (2013.01); *A61B 34/30* (2016.02); *A61B 50/30* (2016.02); *A61B 2017/3407* (2013.01); *A61B 2017/3409* (2013.01); *A61B 2046/205* (2016.02)

(58) Field of Classification Search
CPC .... A61B 2017/3407; A61B 2017/3409; A61B 2046/205; A61B 50/30; A61M 5/158
See application file for complete search history.

(56) References Cited

FOREIGN PATENT DOCUMENTS

| | | |
|---|---|---|
| DE | 202012002296 U1 | 3/2013 |
| EP | 0516582 A1 | 12/1992 |
| WO | 2014162217 A1 | 10/2014 |

\* cited by examiner

DEVICE FOR POSITIONING STERILE INSTRUMENTS

BACKGROUND OF THE INVENTION

1. Field of the Invention

The invention relates to a device for positioning of sterile instruments according to the preamble of claim 1, in particular for controlled movement thereof in a robot-assisted surgical procedure at a sterile area around an interventional site.

2. Description of the Related Art

In medical procedures, a sterile atmosphere around the treated body or skin area of the patient is of great importance to prevent infection. For this reason, in hospitals, and especially in the treatment rooms, a high standard of sterility must be ensured, which applies to the patient, the treating staff and the instruments or devices used. Especially with minimal or micro-invasive procedures, such as percutaneous needle puncture, the surgically treated body surface is very small and sometimes even limited to the respective puncture point. Sterility is also required with multiple needle or instrument placement, especially in the environment of the resulting skin puncture.

In a variety of surgical procedures, the use of a remote-controlled robot is advantageous. For example, surgery robots are often used in conjunction with devices that use electromagnetic radiation to determine the precise puncture position on the patient and the correct penetration depth, f. i. by using X-ray devices. In view of dangerous X-rays, treatment persons exposed to radiation are even risking health. Further, the spatial constriction by the X-ray device makes a manual intervention on the patient difficult. In addition, robots and micromanipulators are far superior to the human hand as to high-precision instrument positioning in 3D space. For these and other reasons, robots and remote manipulators are increasingly used e.g. for positioning surgical intervention instruments at targets determined by X-rays, but also to enable high-precision (microsurgical) intervention on the patient. Surgical robots that allow the introduction and manipulation of needles and needle-like (micro) instruments as well as therapeutic and diagnostic (micro) apparatus are suitable for use with imaging techniques (such as CT, C-bow, X-ray, MRI, ultrasound etc.) by the relatively small size of the robots to be suitably used at narrow sites to be treated.

In order to allow an exact placement of the interventional instrument in the imaging area with subsequent image processing of the specific location, the distance between the holders of the robot to the needle should be as short as possible, but this carries the risk of contamination of the resulting puncture by the robot.

Such robots for remote control of accurate punctures on a patient are described, for example, in EP 1 722 698 B1 or U.S. Pat. No. 5,176,689. To avoid contamination around the needle and the puncture site in front of the robot, various possibilities have already been proposed, f. i. to cover the robot or parts thereof. The needle, separated from a protection by the robot, then has a grade of sterility as in the treatment room. Examples of such robotic protection devices are shown in US 2006/0235436 A1 or WO 2014/127984 A1. These embodiments have the disadvantage that at least parts of the robot must be covered in an airtight manner and this protection must be changed after a certain time, being a time-consuming procedure.

WO 2010/121107 A1 discloses a surgical manipulator which is packaged as a whole in a sterile packaging (similarly also in U.S. Pat. No. 6,132,368) and the robot can be controlled in a wireless way. The surgical tool is attached to the outside of the sterile packaging of the manipulator. This arrangement allows for a high degree of sterility of the manipulator, but has the disadvantages of using electromagnetic radiation to manipulate the instrument and placing the surgical tool outside of the sterile package around the manipulator.

Accordingly, it is the object of the invention to provide a simple device, especially for robot-assisted interventions, which allows for highest sterility in a local environment and is not limited to the application of a particular robot type.

SUMMARY OF THE INVENTION

The basic idea of the invention is that a cover or sheath from the environment (incl. robot) sterilizes the surgical tool and the device is designed to maintain the sterile atmosphere in a limited volume around the surgical site. This arrangement allows for a sterile atmosphere, locally at the intervention site, that is not affected by the surgical procedure and the cleanliness conditions outside of the array.

The proposed device is used for positioning, in particular the introduction and manipulation of needles and (micro) instruments and the positioning of therapeutic and diagnostic (micro) apparatus, such as puncture, injection, ablation needles or endoscopes or the like to a patient. The "balloon-like" sheath is sterile at least on its inner side and surrounds a sterile instrument at least partially, preferably completely or mostly. In addition, at least one gas-tight passage is provided at the sheath, which can serve for coupling an instrument holder. Thus, the instrument holder, like the instrument itself, is received in a sterile manner in the envelope-like sheath and can be moved in at least two spatial directions in a controlled manner by movement of the instrument holder outside the sheath. The instrument holder preferably has coupling parts (quick-release fasteners) outside of the sleeve-like sheath to an external manipulator, which may be formed according to the above-cited state of the art, in particular according to EP 1 722 698 B1.

The components of the device may be sterilized in common or separately by known sterilization procedures and can be safely stored in a sterile packaging or transport box. The assembly of the individual components can take place in a sterile environment before the sterilization procedure or directly before the procedure in a sterile environment.

The sterile instrument preferably has at least one needle-shaped tip with which a membrane directed towards the patient can be perforated. To prevent inadvertent perforation of the sterile sheath, the instrument tip can be fitted with a cap, which can be pushed-off via the sheath before intervention. The attachment of the sheath on the patient, more precisely at the point of intervention is preferably performed with an adhesive surface. The site of intervention is locally cleaned prior to surgery, to increase sterility or to complete the cleaning process at the site, wherein the adhesive surface may be provided with antiviral, antibacterial coating. For easier handling of the sterile sheath and simple attachment of the adhesive surface to the patient, the adhesive surface may be reinforced by mechanical structures and may have grip-like protuberances. These reinforcements provide a clean/flat and sterile attachment of the adhesive surface on the patient, even in narrow body regions and in tight spaces.

The sterile instrument held in the shell can also be controlled by a finger or handle, especially for short procedures without prolonged exposure to radiation or when using imaging techniques without radiation exposure (such as ultrasound or MRI). The handle, in particular at the end opposite the tip, can be arranged outside the sleeve, whereas the main part of the instrument projects into the sheath through a passage. This design is suitable when the sterile instrument is closed at the front end or is a hollow needle, which has a sterile connection to the outside of the sheath for supplying substances in the hollow needle.

As a special embodiment, a membrane is provided in the device, which encloses the instrument at the puncture site in a gas-tight manner. Preferably, the outside of the membrane is covered by at least one peelable protective film, wherein the membrane and/or protective film can be stabilized by a retaining ring, as described above. For detection and spatially referencing of the retaining ring or the protective cover and the instrument in relation to the patient or environment, active or passive markers may be attached to all components of the device. In addition, the sheath preferably includes an inlet valve, which serves to supply sterilizing gas and/or inert gas into the sheath, preferably for generating an overpressure within the sheath, which has a vent for free movement of the "inflated" sheath. The inlet valve or semipermeable membrane can simultaneously serve as a pressure relief valve or outlet valve when placing the instrument.

Of particular importance is the embodiment with an annular adhesive surface for fixing the sheath together with the (sterile) instrument in a gas-tight manner at the surgical site. For this purpose (in addition to the usual disinfection) only the protective film must be removed for rapid provision on the patient. This is supported in that the envelope with adhesive surface and at least one protective film are packaged in a sterile manner together with the instrument in a transport container (see above).

DESCRIPTION OF THE DRAWINGS

An embodiment of the device will be explained in more detail with reference to the drawings. They show in.

DETAILED DESCRIPTION OF THE PREFERRED EMBODIMENTS

Figure 1:
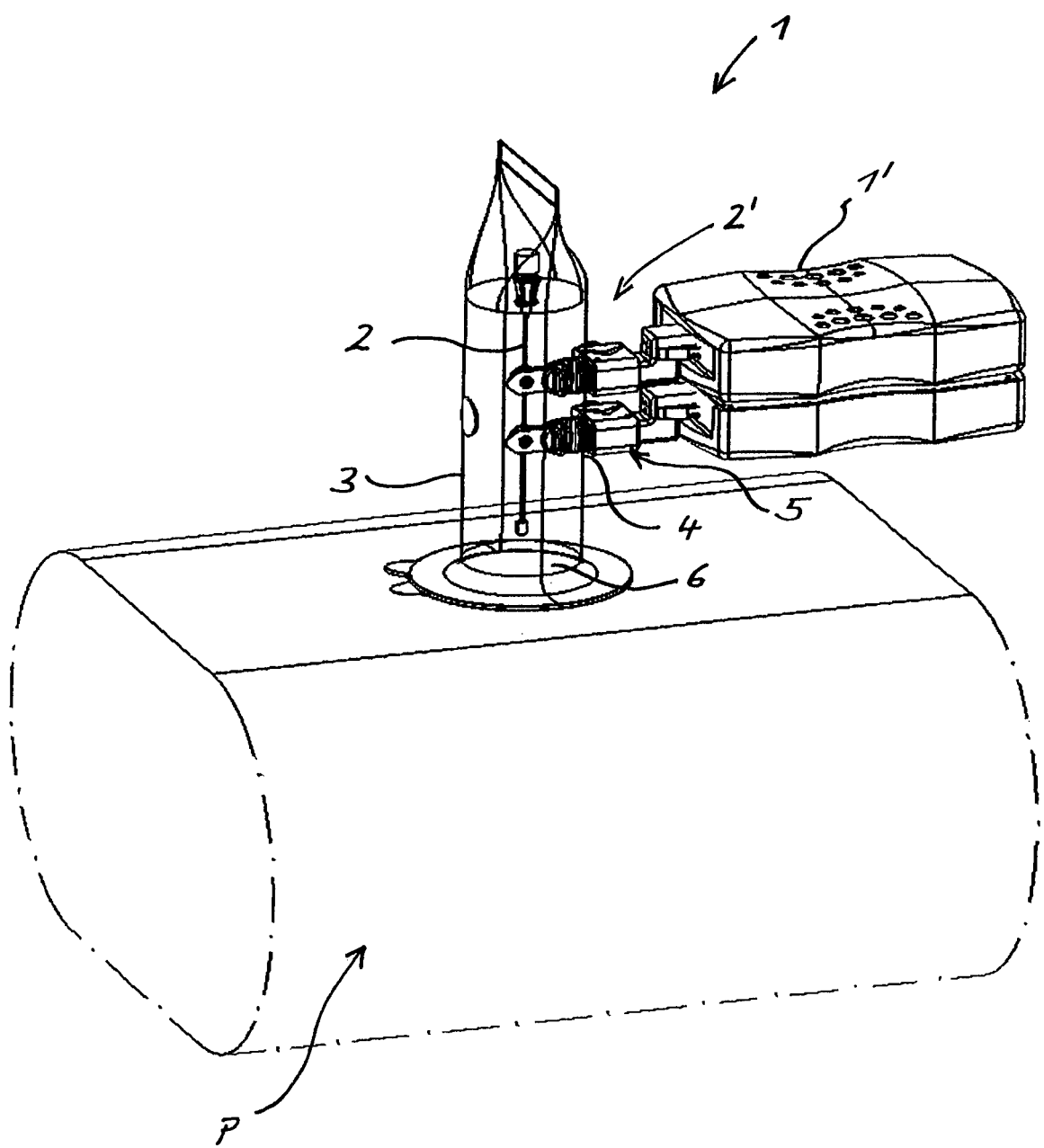
FIG. 1 an overview of the device.

In FIG. 1, a device 1 as described above is placed on a body part of a patient, e.g. on a spine or a knee joint. A sterile instrument 2, for example a puncture needle or injection needle, is attached by means of a likewise sterile holder 2' in a sheath 3, which is sterile at least on its inner side. The sheath 3 is preferably transparent in the manner of a balloon. Gas-tight passages 4 in the sheath 3 connect the sterile instrument holder 2' to coupling parts 5, at which a surgical robot or manipulator 1' can be attached by suitable connections. Thus, the operative tool (instrument 2) within the sterile interior of the sheath 3 can be moved from its outside.

Figure 2:
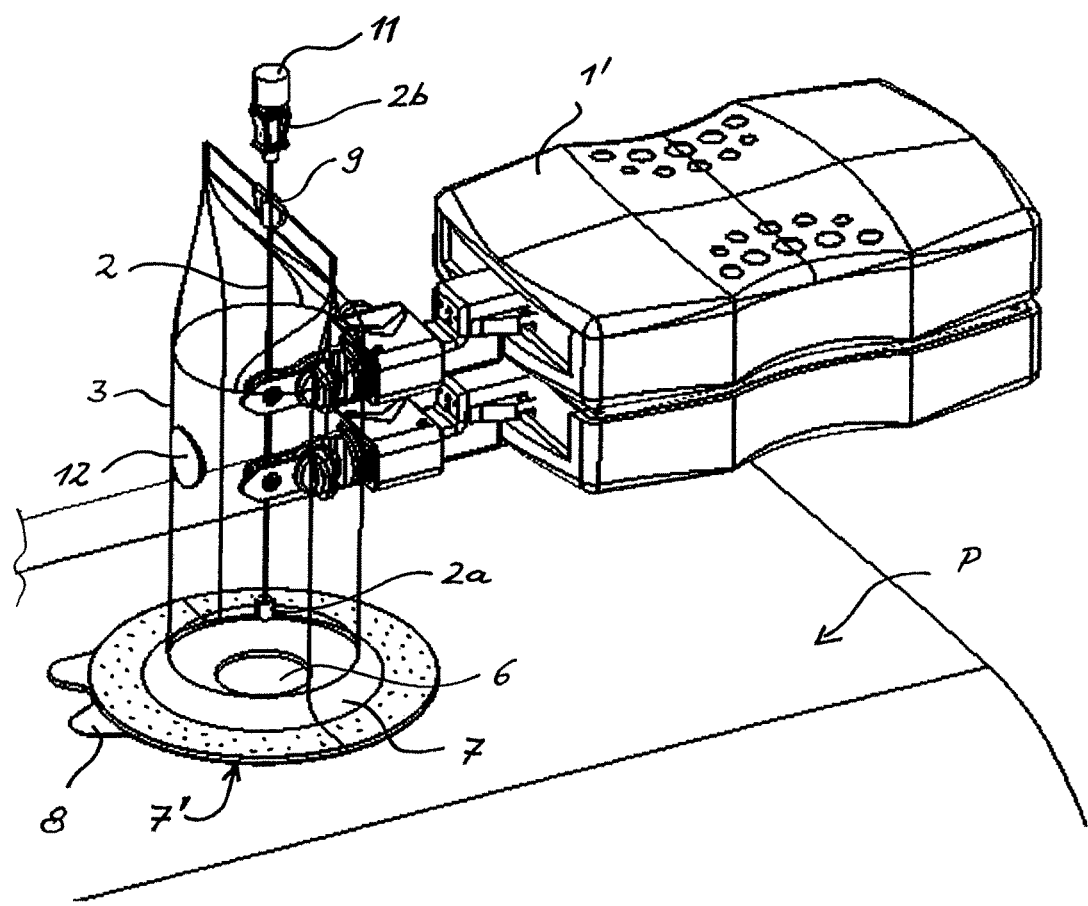
FIG. 2 an enlarged perspective view analogous to FIG. 1.

As shown in FIG. 2, near a tip 2a of the instrument 2 at the lower end of the sheath 3, a membrane 6 may be provided, which can be pierced by the tip 2a (after penetrating or removing a tip protector). The membrane 6 is gas-tightly attached to the sheath 3, similar to the passages 4. A reinforcing or retaining ring 7 for stabilization is further attached to the sheath 3 around the membrane 6 and is fixed to the previously disinfected puncture site of the patient P with a bonding surface 7', shown here in dotted manner. At least one peelable protective film 8 protects the membrane 6 from possible contamination before use.

Opposite to the membrane 6, at the upper end of the shell 3, a gas-tight sleeve 9 is provided as a passage through which the instrument 2 can protrude to the outer space of the sheath 3. The top end of the needle may be provided with a hand or finger grip 2b to move the needle, if necessary, manually and sensitively. A port 11 at the top of the instrument 2 allows drug delivery through a hollow needle to the patient. Optionally, the protruding part of the needle can also be provided with a dome part in order to carry out a robot-controlled movement of the needle, namely an axial feed movement.

Figure 3:
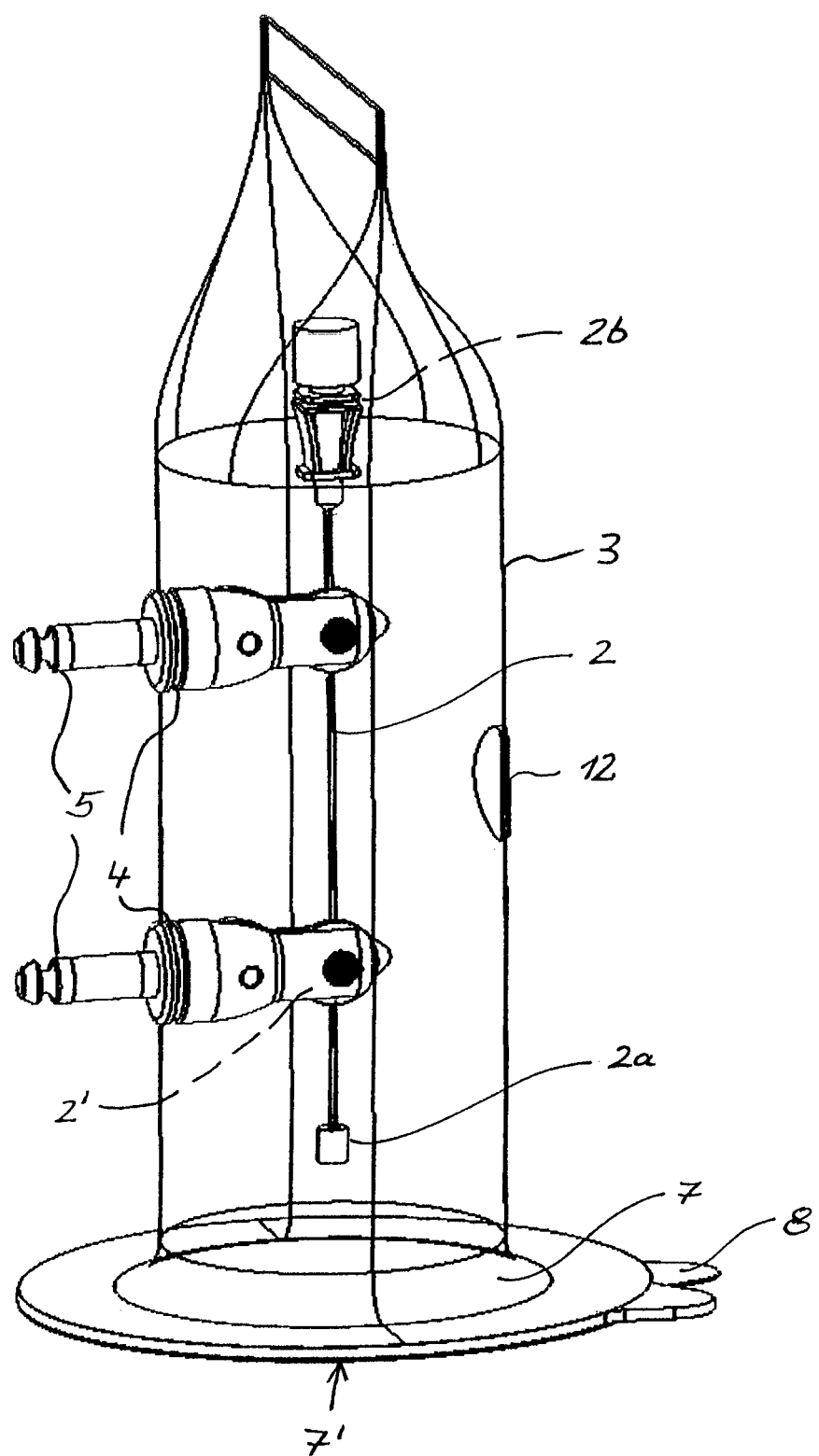
FIG. 3 a further enlargement according to FIGS. 1 and 2.

FIG. 3 shows such coupling members 5 in the form of jack plugs. In order to support the high sterility within the sheath 3, an inlet valve 12 (optionally provided with a filter) may be used for supplying a suitable gas in the sheath 3 to generate a slight overpressure therein, which prevents ingress of germs from outside air during treatment. As a suitable gas, for example, purified air or pure nitrogen may be used. A further opening 13 may be provided at the shell or sheath 3, via which the supplied gas escapes from the sheath 3, for example, if the shell is stabilized by the gas pressure in such a strong way that free movement of the needle 2 relative to the sheath 3 or to the membrane 6 becomes difficult. Disinfections before and after the use of the device 1 can be made by supplying a disinfecting gas through the valve 12. Instead of a valve, semi-permeable shell materials can be used, which allow an inflow or outflow of gases. As an alternative to gas sterilization, gas-free sterilization processes (e.g. irradiation) may be used.

Figure 4:
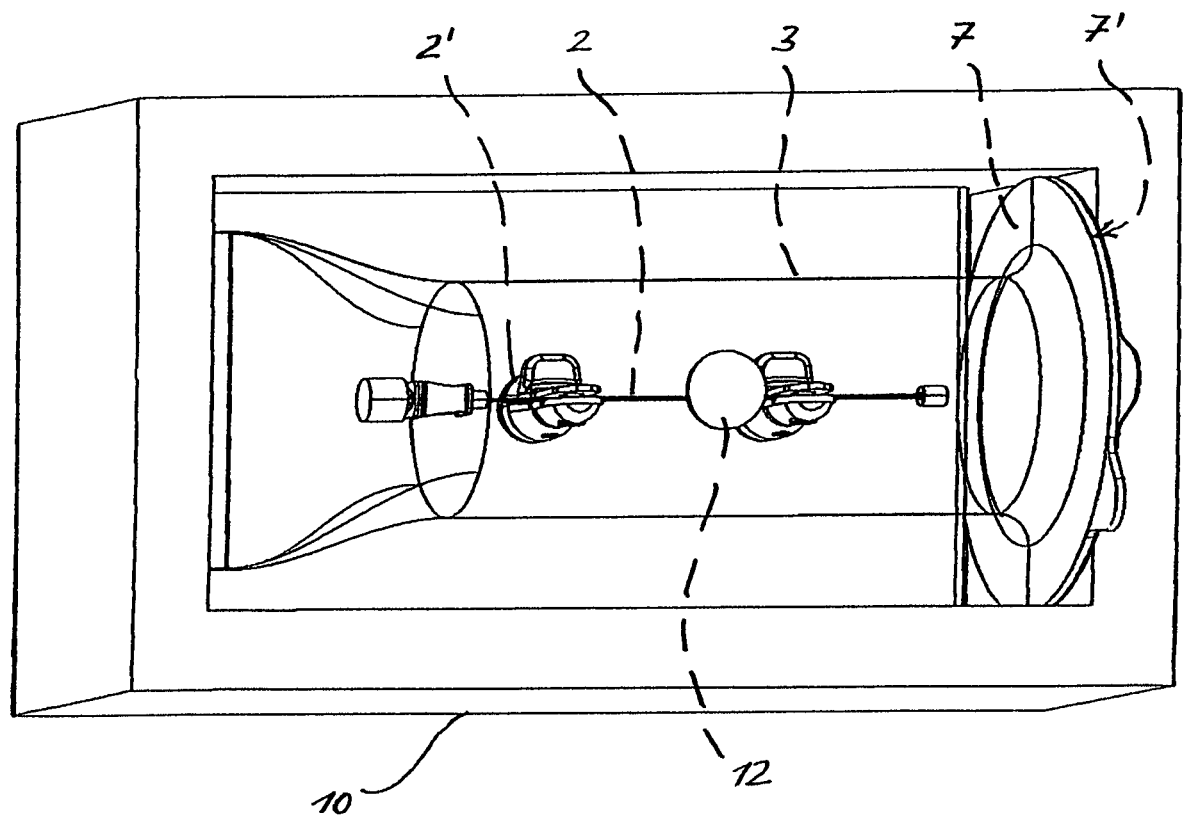
FIG. 4 a transport container for this purpose.

As shown in FIG. 4, the entire device 1 (with sheath 3, instrument 2, etc.) can also be sterilized via the valve 12 and then packaged in a transport container 10. Thus, the components are kept sterile for later intervention on the patient. Thus, the device also allows robot-assisted procedures on a patient in a sterile room created locally around the skin puncture of the patient. The treatment robot, other instruments and persons in the treatment room do not come in contact with the patient and the disinfected needle in contact with the air. This ensures that any problems of sterility in the treatment room have little or no effect on the sterility at the localized treatment point.

In addition to the goal of absolute sterility (infections e.g. by dangerous hospital germs such as MRSA are becoming an increasing problem in hospitals and hospitals hygiene regulations are becoming increasingly stringent) this device should reduce the maximum intervention time and reduce the costs of sterile covers/clothing/disposable items, etc. considerably.

In addition, this device enables the implementation of sterile (micro) invasive procedures, even in non-sterile environments. Especially in countries where there no sterile operating rooms and surgery conditions exist due to lack of money, a multitude of interventions under highest sterility standards becomes possible. Even in richer countries, high hygienic standards in many medical fields are hardly affordable. In particular, in image-based operations many premises do not meet the required hygienic standards. As a result, many rooms either have to be extensively and costly rehabilitated or may no longer be used for (image-based) (robotic) interventions. The proposed device efficiently solves all of these problems in an inexpensive way.

The invention claimed is:

1. Device for positioning a sterile instrument (2), with respect to a patient (P), with a sheath (3) which is sterile at least on its inner side and at least partially enclosing the sterile instrument (2), and with at least one gas-tight passage (4) mounted at the sheath (3), wherein
the sterile instrument (2) has at least one sterile instrument holder (2') which passes through the passage (4) being connected to coupling parts (5) and is movable in a controlled manner in at least two spatial directions by movement of the instrument holder (2') outside the sheath (3), characterized in that the sheath (3) has an annular adhesive surface (7'), directed towards the patient (P), for fixing the sheath (3) together with the instrument (2) on an interventional site in a gas-tight manner.

2. Device according to claim 1, characterized in that the sterile instrument (2) has at least one needle-shaped tip (2a) with which a membrane (6) arranged towards the patient (P) can be perforated after removal of a tip protector.

3. Device according to claim 2, characterized in that the membrane (6) surrounds the instrument (2) at a puncture site in a gas-tight manner.

4. Device according to claim 2, characterized in that the membrane (6) is covered by at least one peelable protective film (8) on the outside of the membrane (6), wherein the membrane (6) is stabilized by a retaining ring (7).

5. Device according to claim 1, characterized in that the has coupling parts (5) that are attachable to an external manipulator (1') outside the sheath (3).

6. Device according to claim 1, characterized in that the sterile instrument (2) has a handle (2b).

7. Device according to claim 1, characterized in that the sterile instrument (2) is a hollow needle, which has a connector (11) outside the sheath (3) for supplying substances into the hollow needle.

8. Device according to claim 1, characterized in that the sheath (3) includes an inlet valve or a semi-permeable membrane (12) for supplying sterilizing gas and/or inert gas into the sheath (3), for generating an overpressure within the sheath (3), and including a venting device.

9. Device according to claim 1, characterized in that the sheath (3) has an annular adhesive surface (7'), directed towards the patient (P), for fixing the sheath (3) together with the instrument (2) on the interventional site in a gas-tight manner.

10. Device according to claim 9, characterized in that the sheath (3) having the adhesive surface (7') and at least one protective film (8) is packaged with the instrument (2) in a transport container (10) in a sterile manner.

11. Device according to claim 1, characterized in that a marker is attached to at least one of the components of the device (1).

* * * * *